(12) United States Patent
Storz

(10) Patent No.: US 7,227,112 B2
(45) Date of Patent: Jun. 5, 2007

(54) METHOD FOR SETTING THE SYSTEM PARAMETERS OF A SCANNING MICROSCOPE

(75) Inventor: Rafael Storz, Heidelberg (DE)

(73) Assignee: Leica Microsystems CMS GmbH, Wetzlar (DE)

(*) Notice: Subject to any disclaimer, the term of this patent is extended or adjusted under 35 U.S.C. 154(b) by 252 days.

(21) Appl. No.: 10/603,310

(22) Filed: Jun. 25, 2003

(65) Prior Publication Data

US 2004/0000639 A1 Jan. 1, 2004

(30) Foreign Application Priority Data

Jun. 29, 2002 (DE) .................................. 102 29 407

(51) Int. Cl.
 G02B 7/04 (2006.01)
 G02B 21/00 (2006.01)
 G01J 1/58 (2006.01)
 H04N 9/47 (2006.01)

(52) U.S. Cl. .............................. 250/201.3; 250/459.1; 359/368; 348/79

(58) Field of Classification Search ............ 250/201.3, 250/234, 235, 208.1, 306, 307, 458.1, 459.1, 250/311; 359/368, 379, 380, 383, 384; 348/79, 348/80, 61
See application file for complete search history.

(56) References Cited

U.S. PATENT DOCUMENTS

| | | | | | |
|---|---|---|---|---|---|
| 5,283,433 | A | * | 2/1994 | Tsien | 250/234 |
| 5,587,832 | A | * | 12/1996 | Krause | 359/385 |
| 6,285,019 | B1 | | 9/2001 | Engelhardt et al. | 250/216 |
| 6,614,452 | B1 | * | 9/2003 | Cable | 715/764 |
| 6,724,419 | B1 | * | 4/2004 | Green et al. | 348/79 |
| 6,859,273 | B2 | * | 2/2005 | Foster et al. | 356/318 |

FOREIGN PATENT DOCUMENTS

DE 19654211 8/1998

* cited by examiner

*Primary Examiner*—Georgia Epps
*Assistant Examiner*—Pascal M. Bui-Pho
(74) *Attorney, Agent, or Firm*—Darby & Darby

(57) ABSTRACT

The present invention concerns a method for setting the system parameters of a scanning microscope, preferably a confocal scanning microscope, acquisition of an image of the specimen performed with the scanning microscope being controlled by a control computer. After an image of the specimen is acquired at least one image quality feature is inputted by a user and is converted by the control computer into at least one system parameter of the scanning microscope.

1 Claim, 5 Drawing Sheets

METHOD FOR SETTING THE SYSTEM PARAMETERS OF A SCANNING MICROSCOPE

CROSS REFERENCE TO RELATED APPLICATIONS

Priority is claimed to German patent application 102 29 407.0, the subject matter of which is hereby incorporated by reference herein.

FIELD OF THE INVENTION

The present invention concerns a method for setting the system parameters of a scanning microscope and a scanning microscope.

BACKGROUND OF THE INVENTION

The invention refers to the field of scanning microscopy, in particular to the field of confocal scanning microscopy. Scanning microscopes have been known from practical use for years. Reference is made in this connection, merely by way of example, to DE 196 54 211 A1. For purposes of the present invention, scanning microscopes are furthermore all microscope types that comprise scanning image detection or image construction. Control computers for such scanning microscopes are usually personal computers that have special interfaces for controlling the microscope hardware. Control computers for purposes of the present invention can also be single-board computers, special computer hardware integrated into the scanning microscope, or an entire computer cluster. Computer clusters serve not only to control the scanning microscope but also to perform farther-reaching calculation-intensive operations, for example the visualization of multidimensional image data. The image data acquired using a confocal scanning microscope usually encompass two-dimensional image data—so-called "optical sections" of a specimen. Depending on the task, three-dimensional image data sets or one-dimensional line scans are also performed, the specimen being confocally illuminated with light of one or more light sources, possibly of different wavelengths. In the case of fluorescence microscopy, single- or multiple-photon processes for exciting the fluorescent markers or specimens are usual.

Confocal scanning microscopes in particular require that the user have sufficient knowledge about the operation of such a scanning microscope, specifically in order to set the mutually dependent system parameters that often also work against one another or are mutually exclusive. These include the pinhole diameter of the confocal detector unit, the high voltage of the photomultiplier (PMT) of the detector unit, the laser power level, etc. For optimum setting of the system parameters, especially in consideration of specimen-specific properties, the user must utilize his or her experience with using such scanning microscopes. Hitherto, however, it has been almost impossible for a user to achieve optimum imaging results without comprehensive relevant experience.

Because of the aforementioned complexity involved in setting confocal scanning microscopes, the operating or system parameters of scanning microscopes are not optimally set by many users. Lack of understanding of the often very complex correlations among various optical and electronic boundary parameters of a confocal scanning microscope is, in particular, the cause of hitherto inadequate operation. But if a scanning microscope of this kind is not optimally set, an image can be acquired only with reduced image quality or with far too long a setting procedure prior to the actual image acquisition. Too long a setting phase prior to the actual image acquisition reduces the efficiency of such a microscope, however, and usually results in excessive wear on the laser light source and/or the light-guiding fibers acted upon by the laser light, and possibly in negative effects on the specimen.

The scanning microscopes hitherto known from practical use are also problematic, in particular, in terms of training new users, since instruction and assistance from experienced users is always necessary. It has hitherto been difficult, however, to learn to use a scanning microscope optimally on a self-taught basis. To the contrary, with existing scanning microscopes an extremely long training phase with the assistance of experienced users is absolutely necessary.

A further problem from existing practice is that many fluorescent specimens become bleached out in the course of very long setting periods. Since long setting periods cannot, however, usually be ruled out, the use of scanning microscopes hitherto known from practical use is limited, especially in the context of biological specimens, and thus problematic. There is thus a need for a reduction in the time required for optimum setting.

SUMMARY OF THE INVENTION

With the aforementioned problems in mind, an object of the present invention is to provide a method for setting the system parameters of a scanning microscope in which a user requires little or indeed no technical knowledge of the effects of the system parameters to be set, and the system parameters are as easy as possible for the user to set.

The present invention provides a method comprising the steps of:
Controlling an acquisition of an image of a specimen with a control computer,
Inputting at least one image quality feature after an image of the specimen is acquired;
Converting the at least one image quality feature into at least one system parameter of the scanning microscope by the control computer; and
Setting the at least one system parameter.

It is another object of the present invention to provide a scanning microscope which allows the system parameters to be set even if the user has little or indeed no technical knowledge of the effects of the system parameters The present invention provides a scanning microscope comprising: a control computer for controlling an acquisition of an image of a specimen with the scanning microscope, an operating console for inputting at least one modified image quality feature after an image of the specimen is acquired, whereby the at least one image quality feature can be converted by the control computer into at least one system parameter of the scanning microscope that can be set.

What has been recognized according to the present invention is that, for example, the learning phase for operation of a scanning microscope can be made considerably shorter for an inexpert user if the user inputs into the control computer, on the basis of a specimen image that has first been acquired, the extent to which he or she wishes to have it modified in a subsequent acquired image. In particularly advantageous fashion, this does not require the user to input the system parameters directly or to accurately know or learn about the technical effects of the system parameters of the scanning microscope. For example, the user specifies that the new image to be acquired is to be "brighter" or "sharper." As a result of this input of an image quality feature, at least one system parameter of the scanning microscope that is to be set in modified fashion is then calculated, and another image can be acquired with modified system parameters of the scanning microscope. Inverse calculation operations are performed in the conversion of image quality features into system parameters, the technical correlations between system parameters and image quality features being taken into account. For example, a calculation is made as to which system parameters of the confocal scanning microscope need to be modified in order to yield the image quality features that are to be set. Thus, advantageously, not only is it possible to shorten a user's learning phase for operation of the scanning microscope, but the entire scanning microscope operation or setting phase can also be made more user-friendly. Ultimately, the user inputs the manner in which the acquired image is to be modified, in that specific case, in terms of its image quality features. After a conversion into system parameters of the scanning microscope, the desired image improvement can be achieved upon acquisition of another image.

The term "image quality feature" is to be understood generally as a property that concerns the quality or the manner of acquisition of the acquired image. Modification of the quality of the acquired image is brought about by means of one or possibly several modified system parameters of the scanning microscope upon acquisition of a new image. For example, an image quality feature could be the image data noise of a detected image, the intention generally being to reduce the noise. The signal-to-noise ratio of the detected image data is also an image quality feature which is relevant, especially in fluorescence microscopy, when only small specimen regions are marked with fluorescent dye and the signal detected therefrom has a value which is close to the noise limit and therefore almost impossible to detect or perceive. In such cases, the signal-to-noise ratio needs to be correspondingly increased. In this context, the bleaching behavior of a fluorescent marking of a specimen, constituting an image quality feature, is also a factor that is recognizable and therefore modifiable by a user.

In many applications it may be necessary to increase the detection speed of the image data set to be detected, for example because the specimen is moving (albeit slowly) relative to the objective. A further image quality feature is, for example, the contrast of a detected image, which needs to be either increased or decreased. In this context, the gamma value is also an image quality feature that similarly needs to be increased or decreased in the context of a gamma correction. If the resolution of the detected image data is insufficient, the resolution, constituting an image quality feature, can be increased by user input. In general terms, all those features that are directly or indirectly recognizable on the basis of the detected image, and that the user wishes to modify, are conceivable as image quality features.

A system parameter of the scanning microscope can be, in particular, the power level of a light source, the wavelength of a light source, the scanning speed of a scanning unit, the diameter of a confocal detection pinhole, the amplifier characteristic of a confocal detector, or the number of individual images to be detected for averaging of an image.

For example, the power level of a light source might be increased when the signal-to-noise ratio of the detected image data are to be modified, or when the bleaching behavior of a fluorescent marking of a specimen permits. A laser light source that emits light of one or more wavelengths usually serves as the light source for a confocal scanning microscope. The power level of a laser light source can be quickly and effectively varied using an acoustooptical tunable filter (AOTF) placed between the laser light source and the scanning microscope. Modification of the wavelength of a light source is necessary in particular for the detection of fluorescent markings of a specimen when certain fluorescent markings are more effectively excited using a different wavelength. In confocal scanning microscopy, a slight variation in the wavelength of a laser light source could be achieved using an optically parametric oscillator (OPO) placed between the laser light source and the scanning microscope. With the OPO, almost any wavelength can be generated continuously on the basis of nonlinear optical processes.

The scanning speed of the scanning unit of the scanning microscope could be increased in particular when a fluorescent marking has pronounced bleaching characteristics. What usually serves as the scanning unit of a confocal scanning microscope is one or more scanning mirrors arranged in the illumination beam path which, by rotation or tilting, deflect the illuminating beam in such a way that the illumination focus scans the specimen (preferably in meander fashion) in the focal plane of the objective. The diameter of a confocal detection pinhole might require enlargement if the signal-to-noise ratio of the detected image data is too low. In a confocal scanning microscope, the diameter of the confocal detection pinhole is directly proportional to the specimen volume in the focal plane of the microscope objective from which reflected or scattered excitation light or fluorescent light is detected. In this context, the amplifier characteristic of a confocal detector might also need to be varied. In a confocal scanning microscope, the detected light is usually detected using a photomultiplier (PMT) associated with the detector. The amplifier characteristic of such a detector is modified, for example, by correspondingly modifying the high voltage applied to the PMT.

Generally, an inputted image quality feature can, upon conversion into system parameters of the scanning microscope, influence or modify several system parameters of the scanning microscope. For example, in the case of a reduction in the "Detected image data noise" image quality feature, the scanning speed of the scanning unit is decreased, and the number of individual images to be detected in order to average a final image is increased. In this case, therefore, two different system parameters of the confocal scanning microscope are modified. The degree to which the two system parameters are to be modified with respect to one another can be determined, for example, on the basis of empirical values stored in the control computer, e.g. in the context of an expert system.

Generally, provision is made that the system parameters of the scanning microscope that are actually set are not outputted or displayed to the user. It may nevertheless be necessary, in individual cases, for the system parameters calculated and presently set by the control computer of the scanning microscope to be outputted and/or displayed to the user for information. In advantageous fashion, such output or display of the presently set system parameters can be used in the context of a training program for operation of the scanning microscope. Specifically, the user receives in this context a response as to which system parameters need to be modified in order to achieve the respective effects (the image quality feature to be modified) upon acquisition of a new image. The goal of such a training program could be that the user ultimately learns to set the system parameters of the scanning microscope directly.

Preferably, the image quality expected to be achievable, for the image quality features presently selected, in the next acquired image is calculated and outputted and/or displayed to the user. Calculation of the achievable image quality can proceed from the new system parameters that are to be set, which have been converted into a new system parameter set on the basis of the image quality features that are desired by the user and are to be modified. This calculation can on the one hand concentrate on purely physical correlations—for example, at a selected resolution and a certain scanning density, a detected image generates "oversampling," i.e. image data redundancies are produced—but on the other hand empirical values (e.g. in the context of an expert system) stored in the control computer can also be utilized. Display or output of the image quality expected to be achieved is preferably accomplished graphically, in particular in color. For example, a region of the user interface of the scanning microscope could be embodied in the form of a traffic light, in which the red light illuminates if the selected system parameter setting is contradictory or results in information losses. A yellow light could illuminate if the calculated system parameters generate artifacts in the next acquired image. A green light could illuminate if the selected system parameter setting appears useful. Successful operation of a scanning microscope is thus possible, in particularly advantageous fashion, with almost no knowledge of the physical or technical effects of the system parameters being set. In addition, as a result of this feature, the imaging process using the scanning microscope can be speeded up to the extent that "bad" images are at least largely eliminated.

Provision could be made that the number of images of the same specimen still expected to be detectable, preferably with the presently set system parameters and at the desired image quality, is outputted and/or displayed to the user. This is helpful especially when acquiring images of fluorescent-marked specimens using a confocal scanning microscope, since as each additional image is acquired, the fluorescent dye can bleach out and the acquired images can thus become unusable. This is advantageous when a three-dimensional image data set of a fluorescent marked specimen is to be acquired, even though it is expected that because of the bleaching behavior of the fluorescent dye, the fluorescent dye will already be bleached out before acquisition of the three-dimensional image data set is complete. In the calculation of the number of images of the same specimen still expected to be detectable, the images of that specimen hitherto detected could be taken into account, with consideration of the system parameter settings applicable in the context of the particular detection. Especially when digital image processing methods are applied here, an improved prognosis can thereby be given as to the number of images still possible. For example, the same image regions of different acquired images having the same marking color might be examined as to their average intensity, with the goal of determining the bleaching behavior of the particular fluorescent dye. The particular system parameter setting is taken into account here when acquiring the respective image.

Generally, provision is made for input of the image quality features by the user to be accomplished using a conventional input unit of the control computer of the scanning microscope, i.e. for example using a computer keyboard and/or a mouse. In order to simplify and/or speed up the process of inputting the image quality features, however, provision could be made for each image quality feature to be set or modified using a control element provided for it. For example, a joystick or a trackball could serve in this context as a control element, and the joystick could have several button elements. In order to modify an image quality feature the user could, for example, press and hold down a corresponding button of the joystick and deflect the joystick to the left or right, thereby bringing about the modification of the image quality feature associated with the button.

According to an embodiment of the present invention, after an image of the specimen is acquired, the user modifies at least one system parameter of the scanning microscope; that acquisition of an image in the context of a modified system parameter or parameters is then simulated; and that the simulation result is outputted and/or displayed to the user.

The strategy hereby pursued for setting the system parameters of the scanning microscope is based on the fact that upon a modification of the system parameters after an image has been acquired, instead of acquiring a new image with modified system parameters, as is usual, firstly acquisition of an image with modified system parameters is simulated, i.e. in this method step a further image is not yet acquired. The result, in advantageous fashion, is that the specimen to be detected is not stressed by a further image acquisition. Instead, the user obtains a simulated image of the specimen already detected at a modified system parameter setting, and can then decide whether to image the specimen with the scanning microscope again at the present system parameter setting that serves as the basis for the simulation. If not, the user will vary at least one further system parameter and the method steps will repeat. In advantageous fashion, provision could be made that, in order to modify the system parameters of the scanning microscope, prior to a simulation of an image acquisition the user inputs an image quality feature that is converted into at least one system parameter of the scanning microscope to be set in modified fashion. The method steps according to claim 1 through 10 could in this respect be combined with the method according to claim 11, for example by the fact that a system parameter modification is brought about by the input and conversion of image quality features.

The simulation could encompass the optical imaging process of the scanning microscope, the simulation preferably being based on the image of the specimen already detected. The imaging properties of the scanning microscope, which either have been determined experimentally or are defined by way of a mathematical description, and which describe the actual imaging behavior of the scanning microscope with sufficient accuracy, could be utilized for simulation of the optical imaging process of the scanning microscope. A mathematical description of this kind could, for example, represent the optical transfer function of the scanning microscope in the form of the three-dimensional point-spread function. If the simulation is based on the image of the specimen already detected, all that is calculated in the context of the simulation is the influence exerted by the modified system parameters on a further detection of the same specimen.

On the basis of the simulation result, the user can decide whether a further image acquisition is to be performed with the scanning microscope using the system parameters now set, or whether a previously modified system parameter is to be even further modified, and/or whether another system parameter is additionally to be modified. With this procedure, the user can thus modify the system parameters of the scanning microscope, without actually acquiring additional images, until the desired final image is identified (at least on a simulated basis). It is thereby possible, in advantageous fashion, to avoid stress on the specimen due to the acquisition of images that are unnecessary or are required only in order to set the system parameters of the scanning microscope. In additionally advantageous fashion, the effect of modifying the system parameters can be integrated, on the basis of the simulation result, in the context of a training program for operation of a scanning microscope.

The simulation of image acquisition with modified system parameters could be accomplished on the control computer of the scanning microscope and/or on a further computer connected thereto. In the case of calculation-intensive simulation calculations in particular, it may be necessary to distribute the calculations among several computers so that the control computer of the scanning microscope is not overloaded by the simulation calculation. For example, the additional computer or computers could be connected to the control computer of the scanning microscope via a network, building on network protocols and parallelization programs that already exist.

Embodiments of the method according to the present invention can be implemented substantially in the context of the control program of the scanning microscope, and scanning microscopes that already exist or have been delivered could be upgraded with the method according to the present invention. In an embodiment of the present invention a scanning microscope, preferably a confocal scanning microscope, is employed for carrying out a method according to the present invention. To avoid repetition, the reader is referred to the general portion of the description.

BRIEF DESCRIPTION OF THE DRAWINGS

There are various ways of advantageously embodying and developing the teaching of the present invention. In conjunction with the explanation of the preferred exemplary embodiments of the invention with reference to the drawings, an explanation is also given of generally preferred embodiments and developments of the teaching. In the drawings:

FIG. 4b schematically depicts a simulated image in the context of a modified system parameter setting based on the image in FIG. 4a.

DETAILED DESCRIPTION OF THE INVENTION

Figure 1:
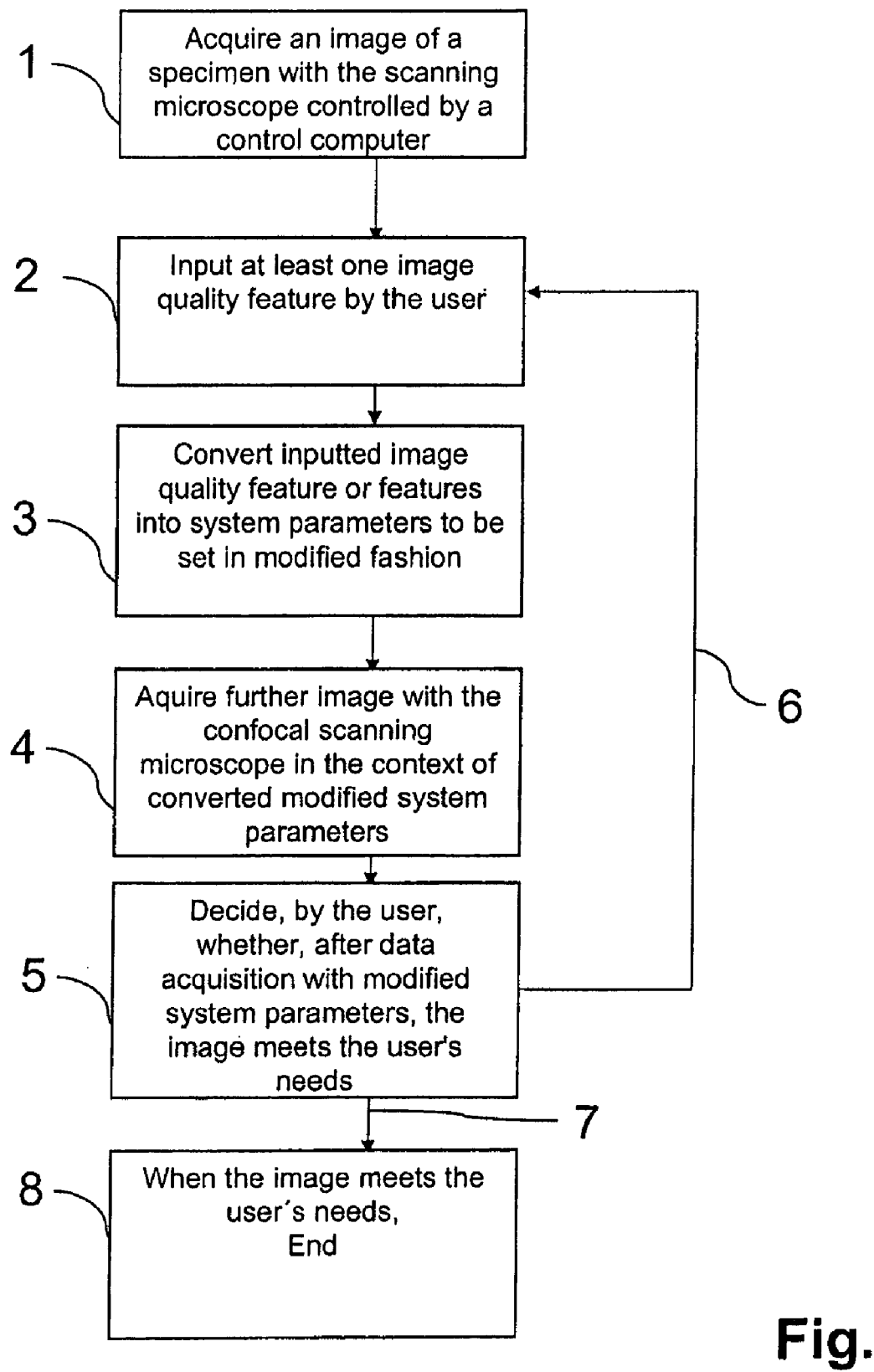
FIG. 1 schematically depicts a flow chart of a first exemplary embodiment of the method according to the present invention.

FIG. 1 shows a flow chart of a first exemplary embodiment of the present method for setting the system parameters of a confocal scanning microscope. Acquisition of an image of a specimen performed with the scanning microscope is controlled by a control computer, the method step of acquiring a first image being labeled with the reference character 1 in the flow chart of FIG. 1. Acquisition of this image is based on a specified system parameter set.

According to the present invention, in the method step having reference character 2 shown in the flow chart of FIG. 1, the user inputs at least one image quality feature. According to method step 3, the inputted image quality feature or features is/are converted into system parameters to be set in modified fashion. With method step 4, a further image is acquired with the confocal scanning microscope in the context of converted modified system parameters. In method step 5, the user decides whether, after data acquisition with modified system parameters, the image meets the user's needs. If such is not the case, then according to branch 6, method steps 2 through 5 are performed again. Otherwise the method for setting the system parameters of the confocal scanning microscope ends, as shown by branch 7, at method step 8.

Figure 2:
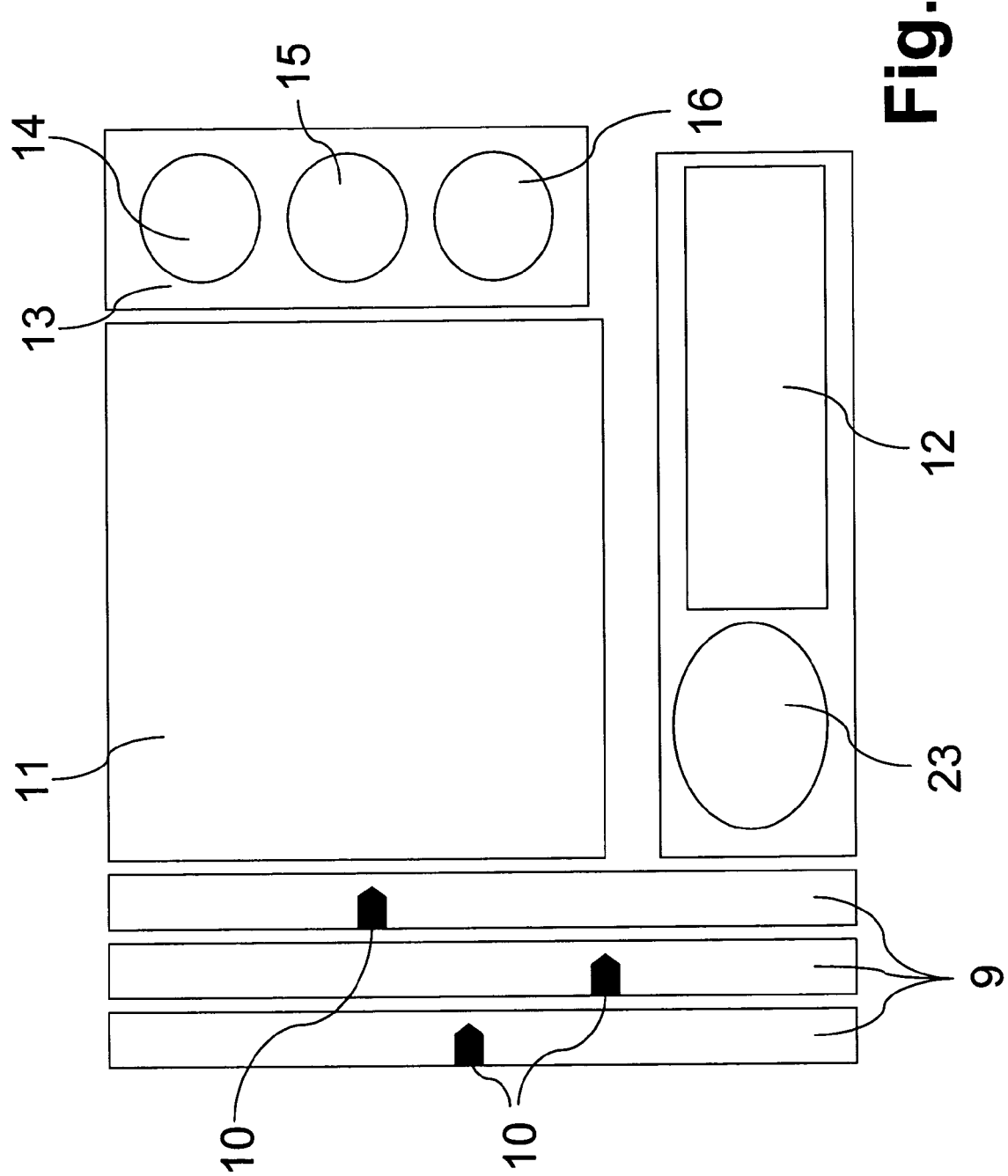
FIG. 2 schematically depicts an operating and output console of the control program of a confocal scanning microscope for carrying out the method according to the present invention.

FIG. 2 schematically depicts an operating and output console of the control program of the confocal scanning microscope for carrying out the method according to the present invention. Shown here on the left are three slider bars 9, each serving to set an image quality feature. Slider bars 9 encompass arrow symbols 10 which indicate the value of the image quality features that are presently set, and with which the respective image quality feature is modifiable, for example using a mouse cursor (not shown). The image acquired in each case is depicted in preview window 11. Output area 12 serves to display the converted or presently set system parameters of the confocal scanning microscope in the context of the particular data acquisition.

Display 13 serves to output the image quality expected to be achieved in the context of the image quality features, presently selected or set, in the context of which image acquisition using the scanning microscope is to be accomplished. Three different areas 14, 15, and 16 are provided here. Area 14 is illuminated in red if the selected system parameter setting is expected to be contradictory or leads to information losses. Area 15 is illuminated in yellow if the selected system parameter setting is expected to generate artifacts. A green indication is given in area 16 if the selected system parameter setting appears useful.

In output area 12, the number of images of the same specimen still detectable, at the present system parameter setting and at the desired image quality, before the specimen becomes unusable as a result of image acquisition is additionally displayed or outputted to the user.

Figure 3:
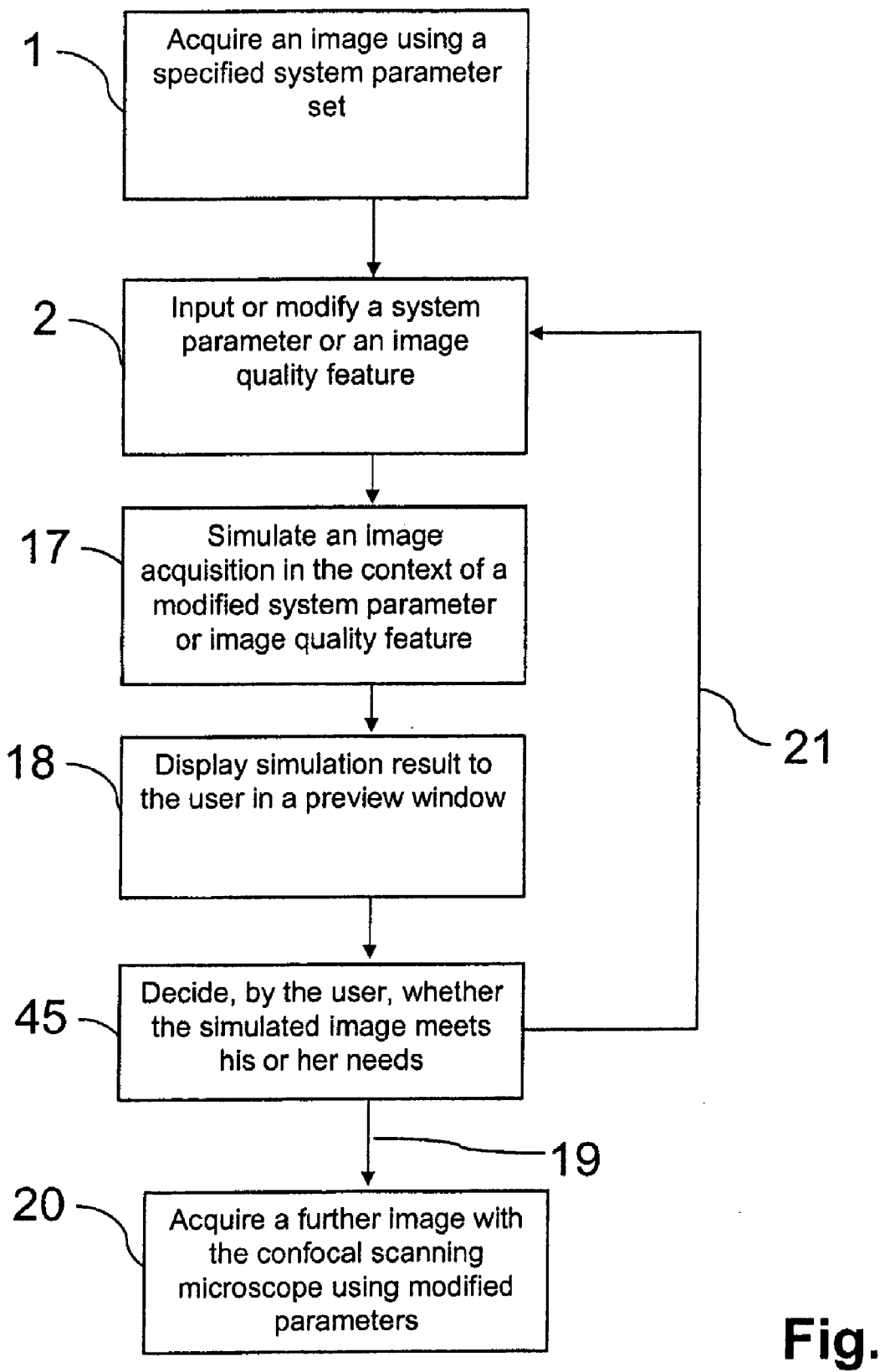
FIG. 3 schematically depicts a flow chart of a second exemplary embodiment of the method according to the present invention.

FIG. 3 shows a flow chart of a further exemplary embodiment of the present method for setting the system parameters of a confocal scanning microscope. As also in the case of the flow chart of FIG. 1, reference character 1 of FIG. 3 refers to the first method step in which an image is acquired using a specified system parameter set. The method step labeled with reference character 2 in FIG. 3 represents the input or modification of a system parameter or an image quality feature. The method step labeled with reference character 17 encompasses simulation of an image acquisition in the context of a modified system parameter or image quality feature. The optical imaging process of the confocal scanning microscope is simulated here, digitally and on the basis of the image detected in method step 1, in conjunction with the optical transfer function of the confocal scanning microscope. In method step 18, the simulation result of method step 17 is displayed to the user in preview window 11 of FIG. 2. In method step 5 of FIG. 3, the user decides whether the simulated image meets his or her needs. If so, a further image is acquired with the confocal scanning microscope using modified system parameters, as shown by branch 19, in method step 20. For that purpose, the user actuates actuation field 23 of FIG. 2, for example using a mouse cursor (not shown). In all other cases, method steps 2, 17, 18, and 5 are cycled through again as shown by branch 21.

Figure 4A:
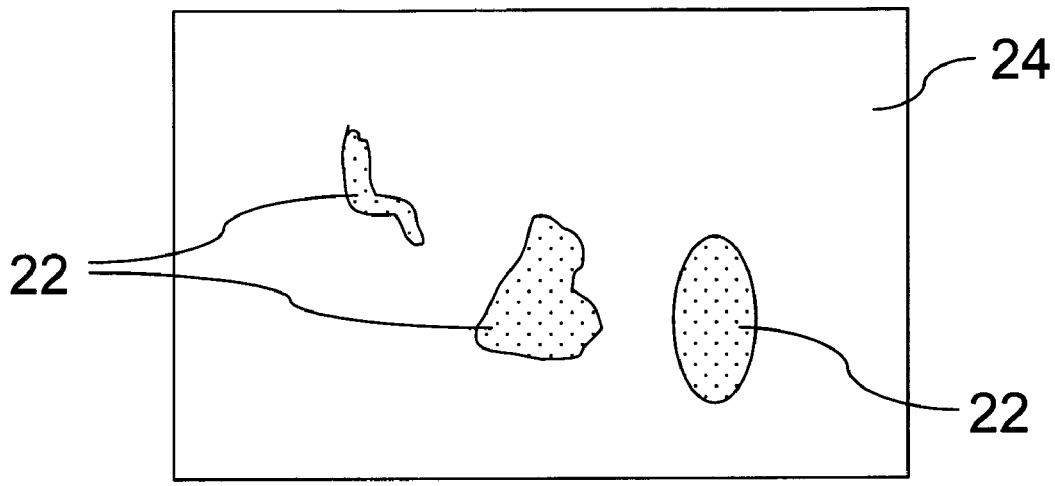
FIG. 4a schematically depicts a detected image of a specimen in the context of a specified system parameter setting.
Figure 4B:
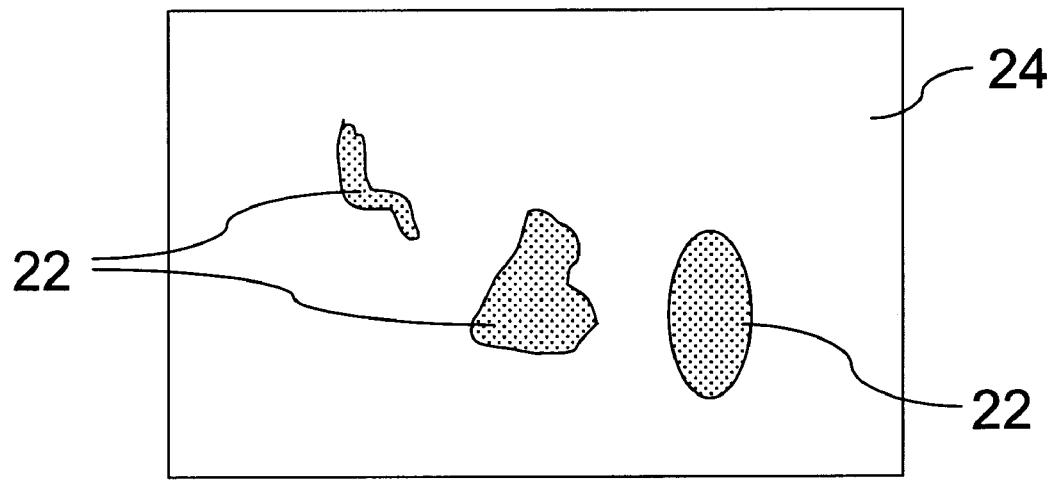
Figure 4C:
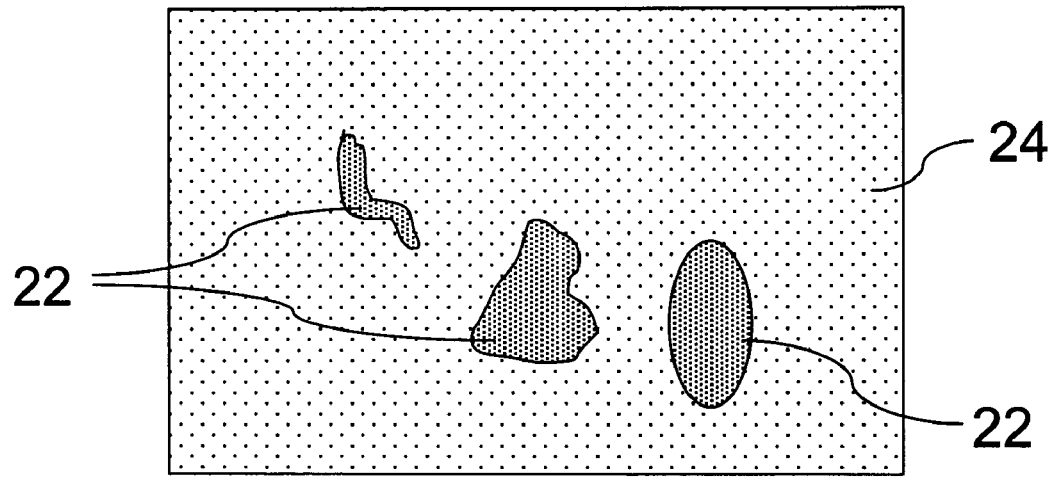
FIG. 4c schematically depicts a further simulated image in the context of a system parameter setting modified further from FIG. 4b.

FIGS. 4a through 4c show different acquired images of three specimens 22, the three specimens 22 having been imaged several times. The image shown in FIG. 4a was imaged, in accordance with method step 1 of FIG. 1, in the context of a specified system parameter set. After the user increased the "Contrast" image quality feature in accordance with method step 2 of FIG. 1, the image shown in FIG. 4b was acquired in accordance with method step 4 of FIG. 1. The "PMT high voltage" system parameter was raised in this context. The denser shading of specimens 22 in FIG. 4b as compared to FIG. 4a indicates in purely schematic fashion that the image contrast has now in fact been increased. After the user increased the "Contrast" image quality feature once again, the image shown in FIG. 4c was acquired. It is indicated in purely schematic fashion that the three specimens 22 have even denser shading, ultimately corresponding to an increased image value or gray value. The shading of image background 24 of the image shown in FIG. 4c indicates that the noise component is now too great, i.e. that another change in system parameters, in accordance with method steps 2 through 5 of FIG. 1, is necessary.

Figure 5:
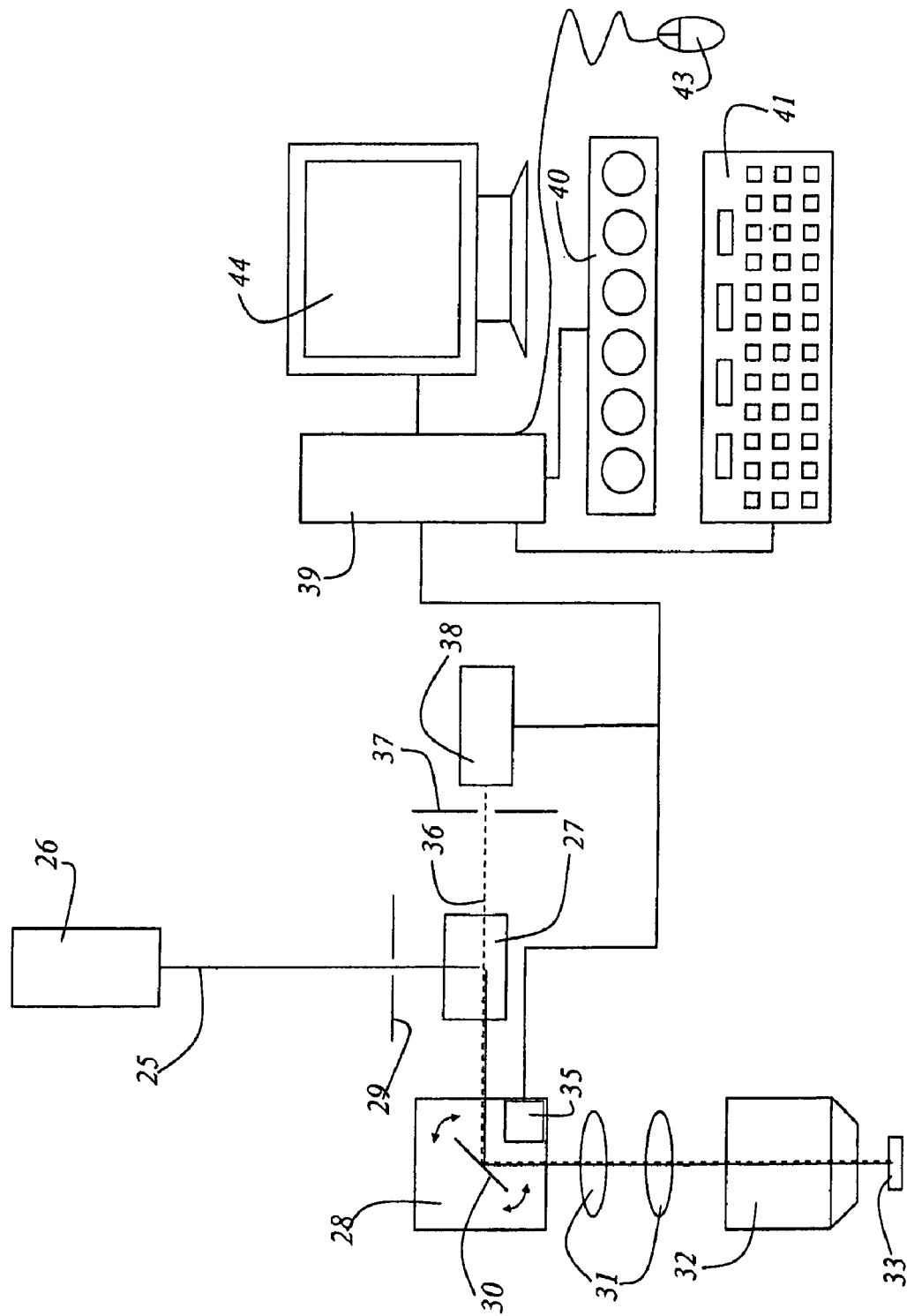
FIG. 5 schematically shows an exemplary embodiment of a confocal scanning microscope.

FIG. 5 schematically shows an exemplary embodiment of a confocal scanning microscope. This is not, however, to be construed as a limitation of the invention. It is sufficiently clear to one skilled in the art that the invention can also be implemented with a conventional scanning microscope. Illuminating light beam 25 coming from at least one illumination system 26 is directed, by a beam splitter or a suitable deflection means 27, to a scanning module 28. Before illuminating light beam 25 strikes deflection means 27, it passes through an illumination pinhole 29. Scanning module 28 encompasses a gimbal-mounted scanning mirror 30 that guides illuminating light beam 25 through a scanning optical system 31 and a microscope optical system 32 and over or through a specimen 33. In the case of non-transparent specimens 33, light beam 25 is guided over the specimen surface. With biological specimens 33 (preparations) or transparent specimens, light beam 25 can also be guided through specimen 33. For these purposes, non-luminous preparations are prepared, if applicable, with a suitable dye (not depicted, since it is established existing art). This means that different focal planes of the specimen 33 are scanned successively by illuminating light beam 25. A position sensor 35 that determines the positional data of the acquired image data is connected to scanning module 28. Subsequent combination of the positional data and image data then yields a two-or three-dimensional frame (or image) of specimen 33. Illuminating light beam 25 coming from illunination system 26 is depicted as a solid line. The light proceeding from specimen 35 defines a detected light beam 36. This travels through microscope optical system 32, scanning optical system 31, and via scanning module 28 to deflection means 27, passes through the latter, and arrives via a detection pinhole 37 at at least one detector 38, which is embodied as a photomultiplier. It is clear to one skilled in the art that other detection components, e.g. diodes, diode arrays, photomultiplier arrays, CCD chips, or CMOS image sensors, can also be used. Detected light beam 36 proceeding from or defined by specimen 33 is depicted in FIG. 5 as a dashed line. In detector 38, electrical detected signals proportional to the power level of the light proceeding from specimen 33 are generated. The data generated by detector 38 are forwarded to a control computer 39, which is connected to an operating and output console 40 of the control program of the confocal scanning microscope for inputting at least one modified image quality feature. The control computer 39 controls the acquisition of images of a specimen 33 with the scanning microscope. The operating and output console 40 includes a keyboard 41 as a setting apparatus 41 for the components of the microscope system. Additionally associated with control computer 39 is an input means that comprises e.g, and a mouse 43. A display 44 is connected to the control computer 39 as a part of the operating and output console 40. At least one image quality feature can be converted by the control computer 39 into at least one system parameter of the scanning microscope that can be set.

In conclusion, be it noted particularly that the exemplary embodiments discussed above serve merely to describe the teaching claimed, but do not limit it to the exemplary embodiments.

What is claimed is:

1. A method for setting the system parameters of a scanning microscope comprising the steps of:

Controlling an acquisition of an image of a specimen with a control computer;

Inputting at least one image quality feature after an image of the specimen is acquired, the at least one image quality feature including at least one of a noise of detected image data, a signal-to-noise ratio of the detected image data, a bleaching behavior of a flourescent marking of a specimen, a detection speed of an image data set to be detected, a contrast, and a resolution;

Converting the at least one image quality feature into at least one system parameter of the scanning microscope by the control computer, the at least one system parameter including at least one of a power level of a light source, a wavelength of the light source, a scanning speed of a scanning unit, a diameter of a confocal detection pinhole, an amplifier characteristic of a confocal detector, and a number of individual images to be detected for averaging of an image; and Setting the at least one system parameter;

wherein an image quality expected to be achievable, for the at least one inputted image quality feature, is calculated in the next acquired image and outputted to the user; and wherein an inputted image quality feature, upon conversion into system parameters of the scanning microscope, influences or modifies several system parameters of the scanning microscope.

* * * * *